(12) United States Patent
Kjonaas

(10) Patent No.: US 6,745,411 B1
(45) Date of Patent: Jun. 8, 2004

(54) SPA SYSTEM

(76) Inventor: Roger L. Kjonaas, 11080-67th St. NW., Bismarck, ND (US) 58503

( * ) Notice: Subject to any disclaimer, the term of this patent is extended or adjusted under 35 U.S.C. 154(b) by 0 days.

(21) Appl. No.: 10/125,193

(22) Filed: Apr. 18, 2002

Related U.S. Application Data

(63) Continuation-in-part of application No. 09/567,173, filed on May 8, 2000, now abandoned.

(51) Int. Cl.$^7$ .............................................. A61H 33/06
(52) U.S. Cl. ............................ 4/524; 607/100; 250/504
(58) Field of Search ................................ 4/524; 607/81, 607/83, 100, 101, 102; 250/495.1, 504; 359/361; 34/266, 267, 268, 269

(56) References Cited

U.S. PATENT DOCUMENTS

| 3,962,504 | A |   | 6/1976  | Sherwin |
|-----------|---|---|---------|---------|
| 5,459,327 | A | * | 10/1995 | Nomura ........................ 250/504 |
| 5,542,194 | A | * | 8/1996  | Hanzawa et al. ............ 34/266 |
| 5,796,076 | A |   | 8/1998  | Azuma |
| 6,004,344 | A | * | 12/1999 | Fujii ........................ 607/100 X |
| 6,117,804 | A |   | 9/2000  | Cho |

FOREIGN PATENT DOCUMENTS

| CA | 1193052   | 9/1985 |
| JP | 60-160957 | 8/1985 |
| JP | 4-129560  | 4/1992 |

* cited by examiner

Primary Examiner—Robert M. Fetsuga
(74) Attorney, Agent, or Firm—Briggs and Morgan, P.A.; Gerald E. Helget; Nelson R. Capes

(57) ABSTRACT

A spa system of the invention includes a room of a structure having a plurality of faces defining a room interior space. A plurality of panels each have a front surface and a rear, with the front surface of each of the panels having an emissivity characteristic with respect to infrared radiation of from 0 to approximately 0.3. A securing device is provided for securing each of the panels to one of the faces of the room, with the securing device being positioned on the rear of each of the panels. An infrared radiation emitter generates infrared radiation and disperses the radiation about the room interior space. The infrared radiation emitter is positioned in the interior space such that infrared radiation generated by the infrared radiation emitter strikes the front surfaces of the plurality of panels.

3 Claims, 9 Drawing Sheets

SPA SYSTEM

RELATED APPLICATION

This application is a continuation-in-part of my application Ser. No. 09/567,173, filed May 8, 2000.

BACKGROUND OF THE INVENTION

1. Field of the Invention

The present invention relates generally to saunas and more specifically it relates to a spa system for providing a comfortable spa session for the individual without producing high air temperatures that tend to reduce the enjoyment of the spa session and tend to foster the growth of microorganisms in the spa.

2. Description of the Prior Art

Saunas have been in use for many years. Typically, a conventional sauna comprises a closed room having a heat source for heating the body of a user located in the room. One known type of sauna, sometimes referred to as a "wet" sauna, utilizes the heat source to generate steam as a means of transferring heat to the body of the user, and thereby causing the user to perspire. Another known type of sauna is a so-called "dry" sauna that utilizes a heat source to heat the body of the user with little or no steam.

However, the high air temperatures (often 180 degrees Fahrenheit to 220 degrees Fahrenheit) and high humidity generated by the wet saunas make them unsuitable or even unsafe for many people. For example, wet saunas are generally not suitable for individuals with health conditions that can be aggravated by experiencing high air temperatures. In addition, women who are pregnant are advised against the use of wet saunas.

Further, because of the equipment needed to generate the steam employed the wet sauna, the apparatus of the wet sauna often requires permanent or semi-permanent construction of a separate sauna room suitable for containing the heat source and the steam generated by the heat source. These requirements can make the installation of a wet sauna in a private home unfeasible, and thus force those wishing to enjoy the benefits of a sauna to travel to a public club or gym and share the experience with others without privacy.

Another type of sauna, known as an infrared sauna, does not use steam, but typically utilizes infrared radiation generated by infrared emitters to heat the user's body. The walls, ceiling, and floor surfaces of the known infrared saunas are often comprised of materials, such as wood boards, which tend to absorb a significant amount of the infrared radiation that strikes these surfaces. These room surfaces are heated by the absorbed infrared radiation (up to a surface temperature of about 150 degrees Fahrenheit), and the heated room surfaces then in turn heat the air in the room that raises the air temperature in the room. Thus, even though the primary means of heating the user's body in an infrared sauna is through the absorption by the user's body of the infrared radiation, the temperature of the air in the room is still raised significantly—albeit by conduction from the heated room surfaces. The raised temperature of the air in the room makes the sauna less comfortable for the user to enjoy, especially for any extended period of time. Further, the incidental heating of the room surfaces can cause, and accelerate, the growth of undesirable organisms on the room surfaces, especially when the room surfaces are constructed of wood, which is difficult to thoroughly clean because of its porosity.

Various known saunas include U.S. Pat. No. 3,648,299 to Durst; U.S. Pat. No. 3,875,596 to Noda; U.S. Pat. No. 5,628,073 to Popovich; U.S. Pat. No. 4,031,573 to Romanoff; U.S. Pat. No. 4,277,855 to Poss; U.S. Pat. No. 5,416,931 to Wolfenden et al; and U.S. Pat. No. 4,765,000 to Currie.

In these respects, the spa system according to the present invention substantially departs from the conventional concepts and designs of the prior art, and in so doing provides an apparatus primarily developed for the purpose of providing a comfortable spa for the individual without producing high air temperatures that tend to reduce the enjoyment of the spa session.

SUMMARY OF THE INVENTION

In view of the foregoing disadvantages inherent in the known types of saunas now present in the prior art, the present invention provides a new spa system construction wherein the same can be utilized for providing a comfortable spa for individuals to utilize without utilizing high air temperatures and without fostering the growth of micro organisms in the spa.

To attain these advantages, the present invention generally comprises a room of a structure having a plurality of faces defining a room interior space. A plurality of panels each have a front surface and a rear, with the front surface of each of the panels having an emissivity characteristic with respect to infrared radiation of from 0 to approximately 0.3. A securing device is provided for securing each of the panels to one of the faces of the room, with the securing device being positioned on the rear of each of the panels. An infrared radiation emitter generates infrared radiation and disperses the radiation about the room interior space. The infrared radiation emitter is positioned in the interior space such that infrared radiation generated by the infrared radiation emitter strikes the front surfaces of the plurality of panels.

The invention also contemplates a kit for forming a spa in a room that includes a plurality of panels having a front surface and a rear surface, a means for securing the plurality of panels to a face of the room; and at least one infrared radiation emitter positionable in the room for generating infrared radiation toward the front surface of at least one of the panels. The front surface of each of the plurality of panels has an emissivity characteristic with respect to infrared radiation of from 0 to approximately 0.3

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

A primary object of the present invention is to provide a spa system that will overcome the shortcomings of the prior art devices.

A second object is to provide a spa system for providing a comfortable spa for individuals to utilize without being exposed to high air temperatures.

Another object is to provide a spa system that may be constructed within many enclosed areas including closets, rooms and corners of a home.

An additional object is to provide a spa system that provides the benefits of a conventional sauna without the high air temperatures.

A further object is to provide a spa system that can be utilized to retrofit an existing conventional sauna.

Another object is to provide a spa system that utilizes infrared heat to increase the exterior body temperature of the user without significantly increasing the air temperature.

A further object is to provide a spa system that is not conducive for the growth of bacteria and microbes, and thereby creating a sanitary spa environment with low temperatures.

An additional object is to provide a spa system that can be readily adapted to and constructed in rooms of various sizes.

A further object is to provide a spa system that can be removed at any time and reinstalled in a different location.

Another object is to provide a spa system that provides an affordable spa for homeowners to utilize.

A further object is to provide a spa system that is aesthetically attractive.

An additional object is to provide a spa system that converts an enclosed area into a permanent or temporary spa.

A further object is to provide a spa system that has air temperatures lower than approximately 130 degrees.

A further object is to provide a spa system that is cleaner than conventional saunas.

An additional object is to provide a spa system that may utilize heat sensors to monitor the user's exterior body temperature or air temperature in the spa.

Another object is to provide a spa system that is of a simple design and easy to install.

Another object is to provide a spa system that is able to provide heat, color, mirror, sound, and aroma therapies to a user.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
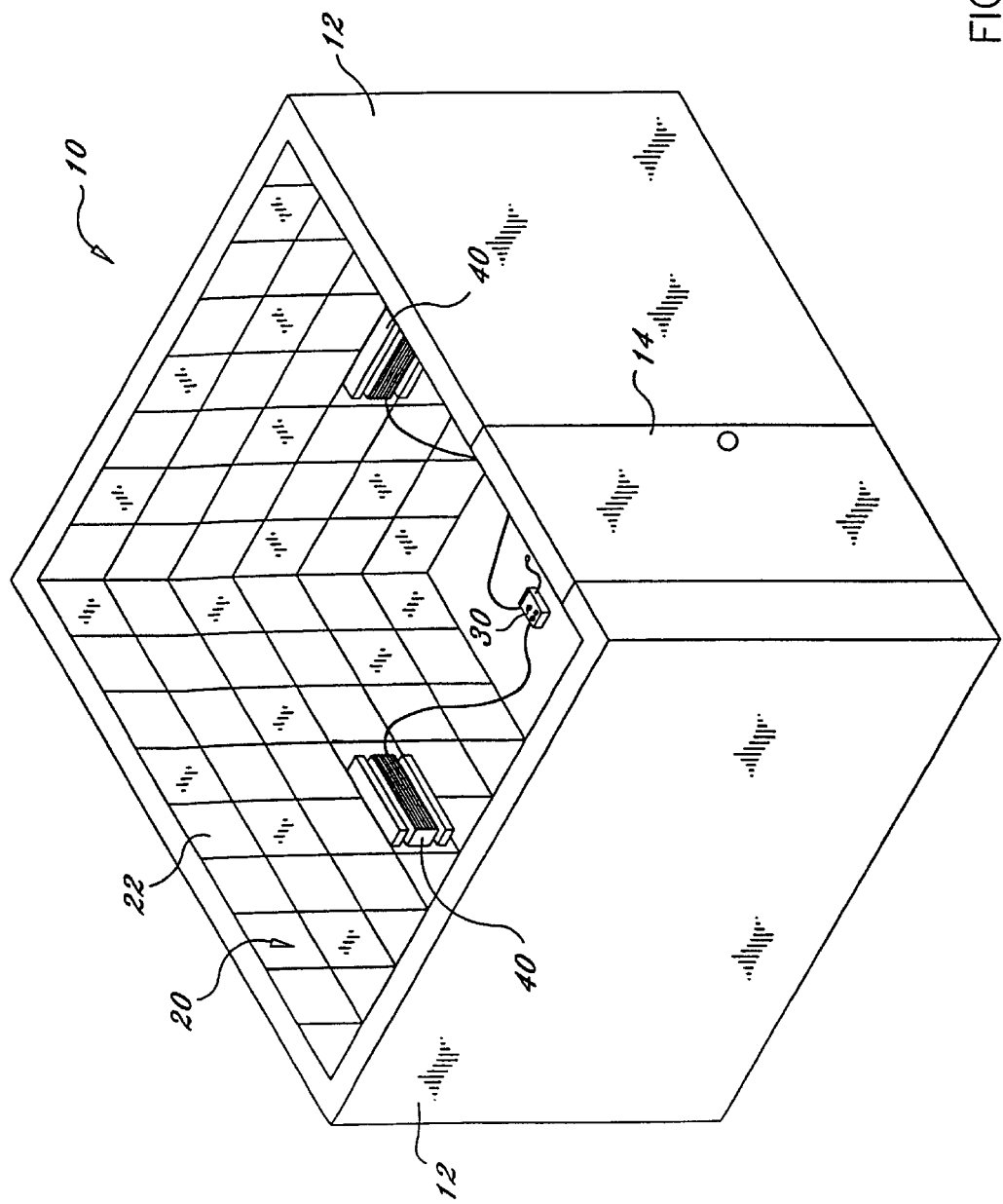
FIG. 1 is an upper perspective view of the present invention positioned in a room.
Figure 2:
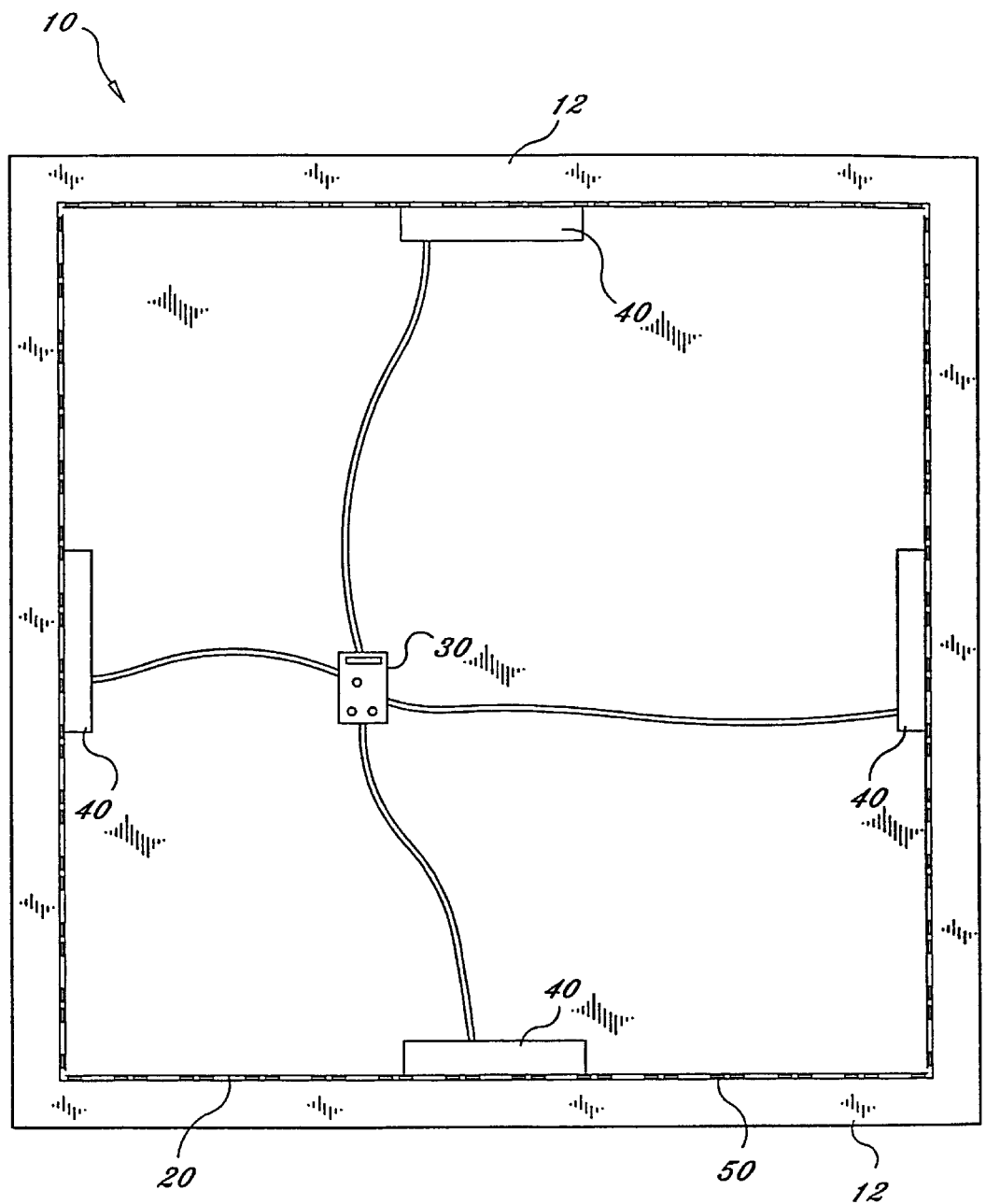
FIG. 2 is a top view of the present invention positioned in a room.
Figure 3:
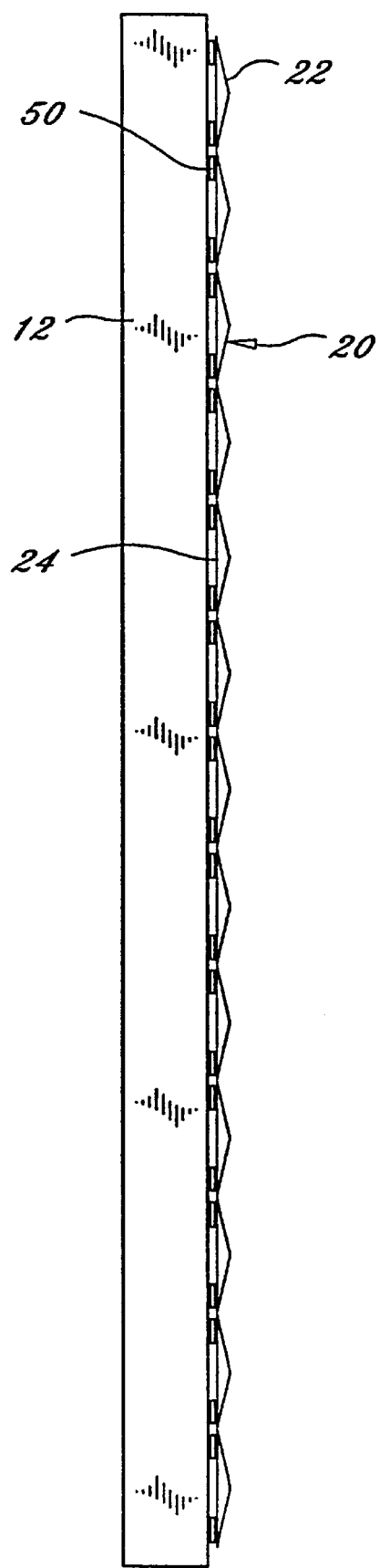
FIG. 3 is a side view of the low emissivity panels of the invention attached to a wall.

With reference now to the drawings, and in particular to FIGS. 1 through 9 thereof, a new spa system embodying the principles and concepts of the present invention and generally designated by the reference numeral 10 will be described.

The spa system of the invention may be employed to create a relaxing and therapeutic environment for the user, and may include therapies such as heat, color, mirror, sound, and aroma. The spa system 10 may be employed and may include a room 11 having a plurality of faces with one or more panels 20, one or more infrared radiation emitters 40, and a control unit 30 electrically connected to the infrared radiation emitters 40.

The spa system 10 is suitably employed in a room, such as a room formed in a structure, and the structure may be immovable (such as a building) or may be movable (such as in a motor home, camper or trailer), and may comprise a self-contained panelized unit. The room 11 may have a plurality of faces 12 that define an interior space of the room. The plurality of faces may include wall faces 13 of the room. In one embodiment, the wall faces 13 may be substantially vertically oriented, and each of the wall faces 13 may be oriented substantially perpendicularly to each of the other wall faces positioned adjacent to the wall face. The room 11 may also include an access door 14 located in one of the wall faces 13 of the room 11. The plurality of faces may also include a ceiling face 15, and the ceiling face 15 may be substantially horizontally oriented, and may extend between upper ends of the wall faces 13 to thereby close an upper end of the room. The room 11 may also have a floor face 16 located in opposition to the ceiling face.

In some embodiments of the invention, the plurality of faces 12 may also include a plurality of transition faces 17, with each of the transition faces 17 extending between a pair of adjacent wall faces 13. Thus, the transition faces 17 may bridge across corners of the room formed by adjacent wall faces 13. Each of the transition faces 17 may be angled with respect to the adjacent wall faces 13, and in one embodiment each of the transition faces is positioned at an angle of approximately 45 degrees with respect to each of the adjacent wall faces.

The spa system 10 as contemplated in the invention and applied to a room includes at least one of the faces 11 of the room having or exhibiting a relatively low emissivity characteristic with respect to infrared radiation. The emissivity characteristic is a property of the material on the face or faces of the room that signifies the relative amount, or percentage, of infrared radiation that is absorbed by the face rather than being reflected back into the interior of the room. The low emissivity of the face or faces of a room employing the invention causes a relatively large percentage of the infrared radiation that strikes the face or faces to be reflected back into the interior of the room, while only a relatively small percentage of the infrared radiation is absorbed by the face. It should be understood that the face or faces of the room themselves are not active emitters of infrared radiation, but should passively reflect a large amount of the infrared radiation that is actively emitted by the infrared radiation emitters 40 into the interior of the room.

The emissivity characteristic of the face or faces of the room is relatively low. Critical to the satisfactory function of the spa system is that the emissivity value of the low emissivity face or faces is in the range from 0 to approximately 0.3. Faces exhibiting emissivity values greater than approximately 0.3 are undesirable for the purpose of the spa system of the invention since faces having such high emissivity levels, while exhibiting some reflection of the infrared radiation, will absorb sufficient radiation to become heated by the radiation and then heat air in the room by conduction. The heating of the air in the room is distinguishable from the heating of the user's body by the infrared radiation, as the heating of the body by the infrared radiation occurs deeper in the body (below the skin) of the user than the heating of the surface of the skin of the user by the heated air. The deep heating of the user's body by the infrared radiation is highly preferable to the heating of the surface of the skin by heated air. Heating of the air by the faces of the room, while unavoidable to some degree, can be minimized to a significant degree by employing faces with relatively low emissivity characteristics, at least less than approximately 0.3. For example, in one embodiment of the invention, after approximately 30 minutes of operation, the air temperature in the room raises from approximately 80 degrees Fahrenheit (approximately 27 degrees Celsius) to approximately 105 degrees (approximately 41 degrees Celsius), and a wall face temperature does not exceed approximately 95 degrees Fahrenheit (approximately 35 degrees Celsius). In contrast, conventional wet and dry saunas the air temperature may be raised to temperatures in the range of 180 degrees Fahrenheit (approximately 82 degrees Celsius) to 220 degrees Fahrenheit (approximately 105 degrees Celsius), and conventional infrared saunas not employing the present invention may exhibit air temperatures as high as approximately 150 degrees Fahrenheit (approximately 66 degrees Celsius) and surface temperatures as high as approximately 160 degrees Fahrenheit (approximately 71 degrees Celsius).

Relatively improved performance of the spa system is observed when the emissivity value of the face or faces is in the range from 0 to approximately 0.2, as absorption of the infrared radiation by the faces is further reduced, and when the emissivity value of the face is in the range from 0 to approximately 0.1, the heating of the air is still even further reduced and the performance of the infrared emitters is optimally enhanced since a significant portion of their radiated energy is delivered to the user's body and not the faces of the room. The emissivity characteristic is preferably measured at a typical operating temperature of the spa system, which is in the range of approximately 75 degrees Fahrenheit (approximately 24 degrees Celsius) to approximately 110 degrees Fahrenheit (approximately 44 degrees Celsius).

It will be appreciated that the emissivity of the face may be greatly affected by not only by the material forming the face, but also the surface finish on the face, as relatively smoother and more highly polished surfaces generally have lower emissivity values than rougher finishes. Smoother finishes also have the advantage of being easier to clean when needed.

Some materials having highly suitable infrared emissivity characteristics for use in the invention include stainless steel, steel, aluminum, tin, brass, and silver (including silver-coated) material. Materials having a high resistance to corrosion are the most suitable for the extended use of the invention as these materials are the most likely to maintain a relatively uniform and constant emissivity characteristic during years of use of the system.

In one highly preferred embodiment of the invention, all of the wall faces of the room have a relatively low emissivity characteristic such that a relatively high percentage of the infrared radiation emitted by the infrared emitters is reflected back into the interior of the room where the user is positioned. The relatively low emissivity of opposed and substantially parallel wall faces in the room produces back and forth reflection of the infrared radiation that enhances the amount of infrared radiation available to be absorbed by the user or users in the room. Optionally, for even greater reflectivity of the infrared radiation back into the interior of the room, the ceiling face may also have a relatively low emissivity character for infrared radiation. Significantly, a room with all wall faces and the ceiling face having a low emissivity characteristic exhibits a greater effective emissivity than a room having only one face with the low emissivity characteristic, as the radiation produced by each of the infrared radiation emitters may be "bounced" off of faces more than one time before finally being absorbed by the user or one of the faces. Thus, the geometrical arrangement of the faces having the low emissivity characteristic can also be a significant contributor to maximizing the utilization of the infrared radiation for heating the body of the user or users in the room.

In those rooms having transition faces 17, the transitional faces may also exhibit low emissivity to thus present skewed reflective faces for causing greater movement of reflected radiation through a central area in the room.

In one highly preferred embodiment of the invention, the relatively low emissivity characteristic of the faces of the room is produced by covering the faces with at least one panel 20, and optionally may include a plurality of panels 20 positioned to cover one or more of the faces of the room. Each of the panels has a perimeter edge, and the perimeter edges of each panel of the plurality of panels may be positioned adjacent to the perimeter edge of another panel of the plurality of panels, as shown in FIGS. 1, 5, 8 and 9 of the drawings. Each of the panels 20 has a front surface 22 that is characterized by having a relatively low emissivity characteristic. The employment of multiple panels on a face of the room can facilitate the covering of a variety of wall sizes where one panel per wall would most likely require more specialized or customized fabrication.

The front surface 22 of each panel 20 may be polished to enhance the infrared reflectivity of the front surface, and also enhance the reflectivity of the front surface to visible light wavelengths. This enhanced reflectivity of visible light can facilitate the user's viewing of his or her reflection on a number of the faces of the room, which can enhance the relaxing experience of the user in the room of the spa system, especially in the presence of relatively low lighting levels within the room. It is contemplated that the front surface may also be relatively non-porous such that cleaning of the front surfaces is made easier and more effective to reduce any growth of bacterial and microbes.

The front surface 22 of the panels 20 may be flat and substantially planar, or optionally may be raised or angled or contoured to provide various reflection directions for the infrared radiation.

Each of the panels 20 may also have a rear surface 24. In one embodiment of the invention, the rear surface 24 of the panels 20 is adhered to one of the plurality of faces of the room such that the front surface 22 of the panel is directed inwardly toward the interior space of the room.

Preferably, the plurality of panels 20 are arranged on the faces of the room such that the panels substantially cover each of the desired faces of the room such that the front surfaces of the plurality of panels are substantially continuous about the interior space of the room to minimize exposed areas that may have relatively greater emissivity levels.

Optionally, the panels 20 may be mounted on a floor face of the room, although placement of panels on the floor face has not been found to be necessary for the satisfactory performance of the system in utilizing the infrared radiation emitted. Scratching by foot traffic of the highly polished faces of panels placed on the floor may reduce the effectiveness of the low emissivity character of the panels.

Means may be provided for securing each of the panels to the faces of the room on the rear surface 24 of the panels 10. The securing means may comprise an adhesive, and may be embodied, for example, as a layer or a strip 50 of adhesive, or a piece of tape with adhesive applied to both sides. Optionally, a plurality of adhesive strips 50 may be attached to the rear surface 24. All or a portion of the rear surface 24 of the panels 20 may be flat for receiving the adhesive strips 50 (see FIG. 4). Various types of securing means may also be utilized, such as, for example, silicone, glue, hook and loop fasteners, or hook structures for securing the panels 20 to the faces 12 and optionally the door 14.

The infrared radiation emitter 40 or emitters of the invention disperse infrared radiation waves about the interior space of the room that are reflected by the panels 20 secured to the walls 12 of the room. The infrared radiation emitters may be mounted on the wall faces of the room, and in one highly preferred embodiment of the invention the emitters may be mounted on one or more of the transition faces 17 of the room. The mounting of the emitters 40 on the transition faces 17 positions the emitters so that the infrared radiation and directs the infrared radiation at an angle into the interior of the room so that the radiation waves are more likely to bounce or reflect off of multiple wall faces at angles that are not necessarily perpendicular to the plane of the wall faces.

The control unit 30 is electrically connected to the infrared heat emitters 40 for controlling the infrared heat emitters 40.

A skin temperature sensor 42 may be included in the system for detecting the temperature of a user positioned in the interior of the room to inform the user of his or her skin temperature, and optionally may be connected to the control unit 30 to shut off the infrared emitters 40 when a predetermined skin temperature of the user is reached or exceeded. The skin temperature sensor 42 may be mounted on the one of the faces 12 of the room and may be directed inwardly toward a central area of the interior of the room. A display 46 of the temperature detected may also be included for informing the user of his or her current detected skin temperature. A number of suitable noncontact infrared temperature sensors suitable for use in the invention are available from Raytek Corporation of Santa Cruz, Calif.

An air temperature sensor 44 or thermometer may also be positioned in the room and may be electrically connected to the control unit 30 for monitoring the air temperature in the room.

Optionally, the experience provided by the spa system 10 may be enhanced by other therapies including color, mirror, sound, and aroma therapies. The system 10 may include one or more lights 32 positioned in the room 11 that may be illuminated in various colors for providing color therapy in a variety of colors according to the desired effect. In one embodiment of the invention, a pair of lights 32 is mounted on the ceiling face 15 of the room.

Significantly, faces and panels having a very smooth or polished finish tend to be highly reflective of the visible light produced by the lights 32, and faces and panels with these smooth or polished surfaces also tend to have the lowest relative infrared radiation emissivity characteristics. In a related aspect of the invention, the polished finish on the faces or plates may be so highly reflective that the mirror image of the user may be viewed on the surface, which makes the spa system highly useful for the purposes of mirror therapy, which can be useful for relieving depression, treating anorexia, and for facilitating self-affirmation, as well as treating partial paralysis of the body. In such an embodiment of the invention, the capability of performing mirror therapy is combined with a very low infrared emissivity character so that both the mental and the physical aspects of the user may be positively influenced. The greatest visible light reflectivity is typically exhibited by surfaces having emissivity characteristics of values of approximately 0.2 and lower, and is especially strong when the emissivity of the surface is approximately 0.1 and lower.

Further, the system 10 may include means for producing sound in the interior of the room, and may include one or more speakers 34. In one embodiment, the speakers 34 are mounted on the ceiling face 15 of the room. Still further, the system may include an aromatherapy assembly 36. In one embodiment, the aromatherapy structure 36 may include a cup member 38 mounted on top of one of the infrared emitters 40, and an absorptive material 39 may be located in the cup member and periodically sprinkled with an aromatherapy liquid. In one embodiment, the aromatherapy structure 36 may be located adjacent to an air inlet 52 of the room so that incoming for the inlet 52 air passes over and around the structure 36 for enhancing diffusion of the aroma vapors.

Figure 5:
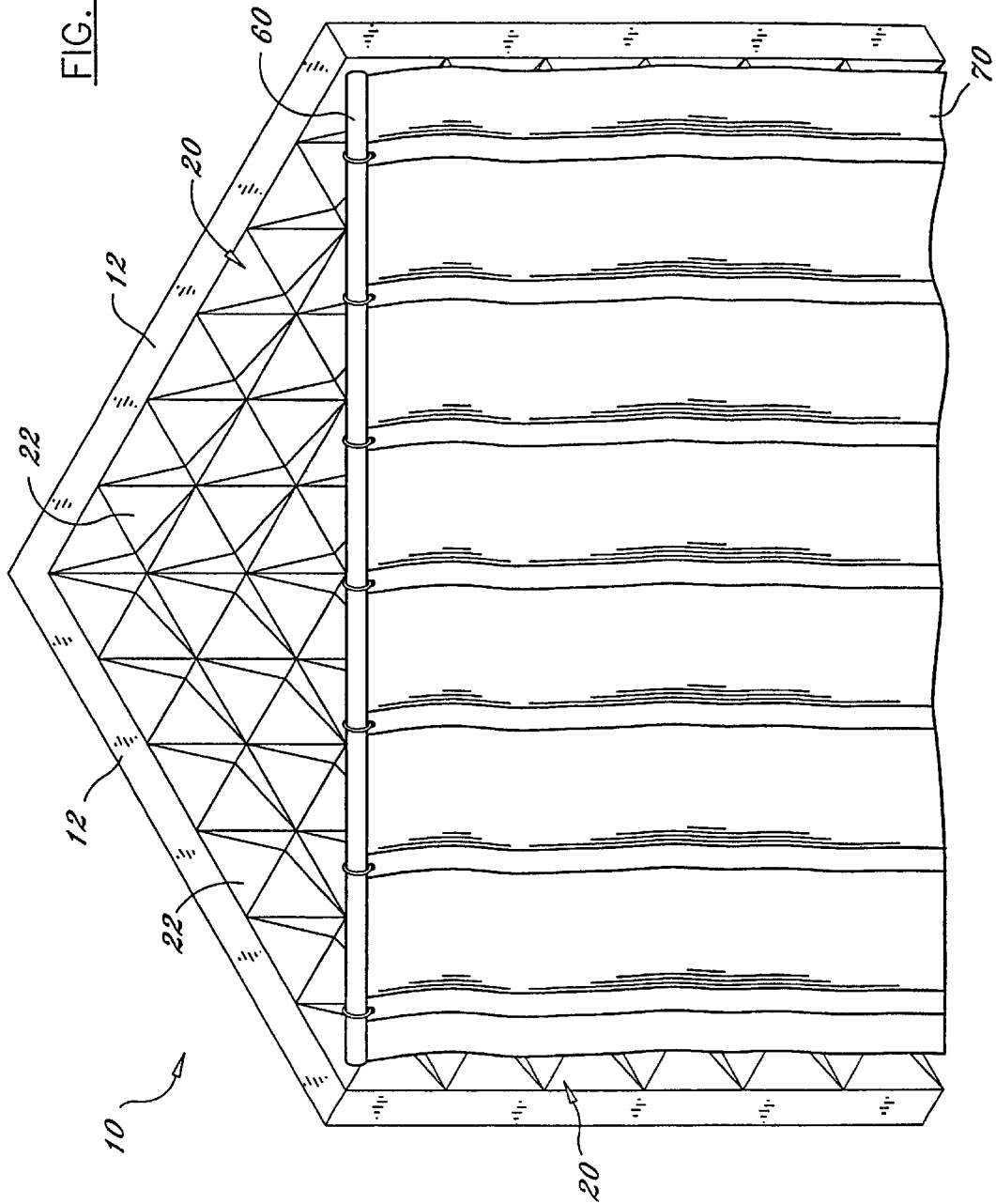
FIG. 5 is an upper perspective view of the present invention using a reflective curtain.
Figure 6:
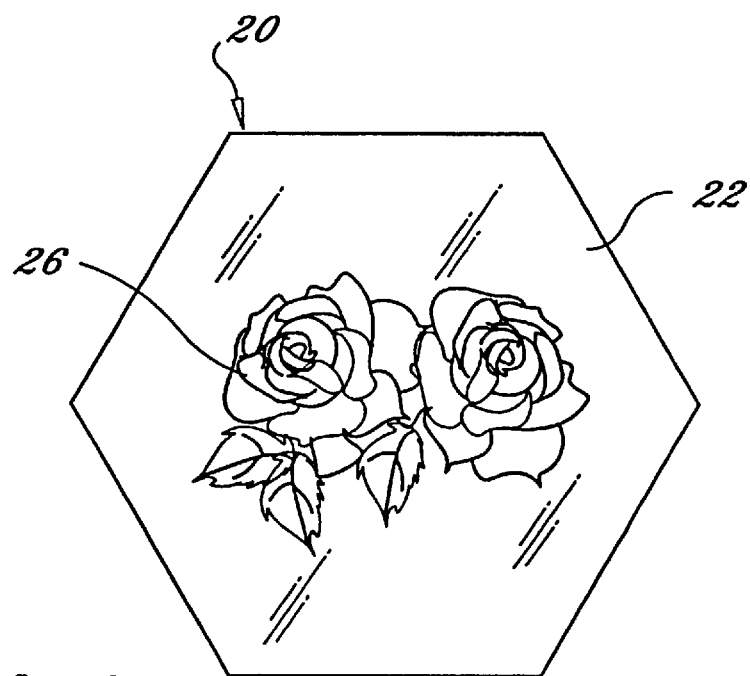
FIG. 6 is a front view of a panel with a design of a different reflective surface inset.
Figure 7:
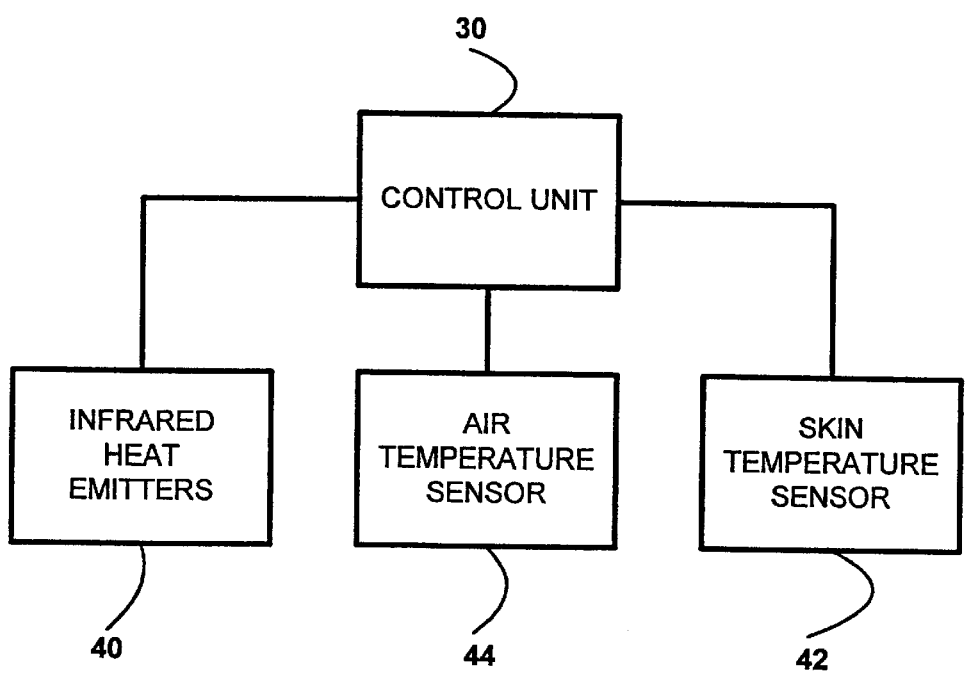
FIG. 7 is a diagrammatic representation of the control elements of the invention.
Figure 8:
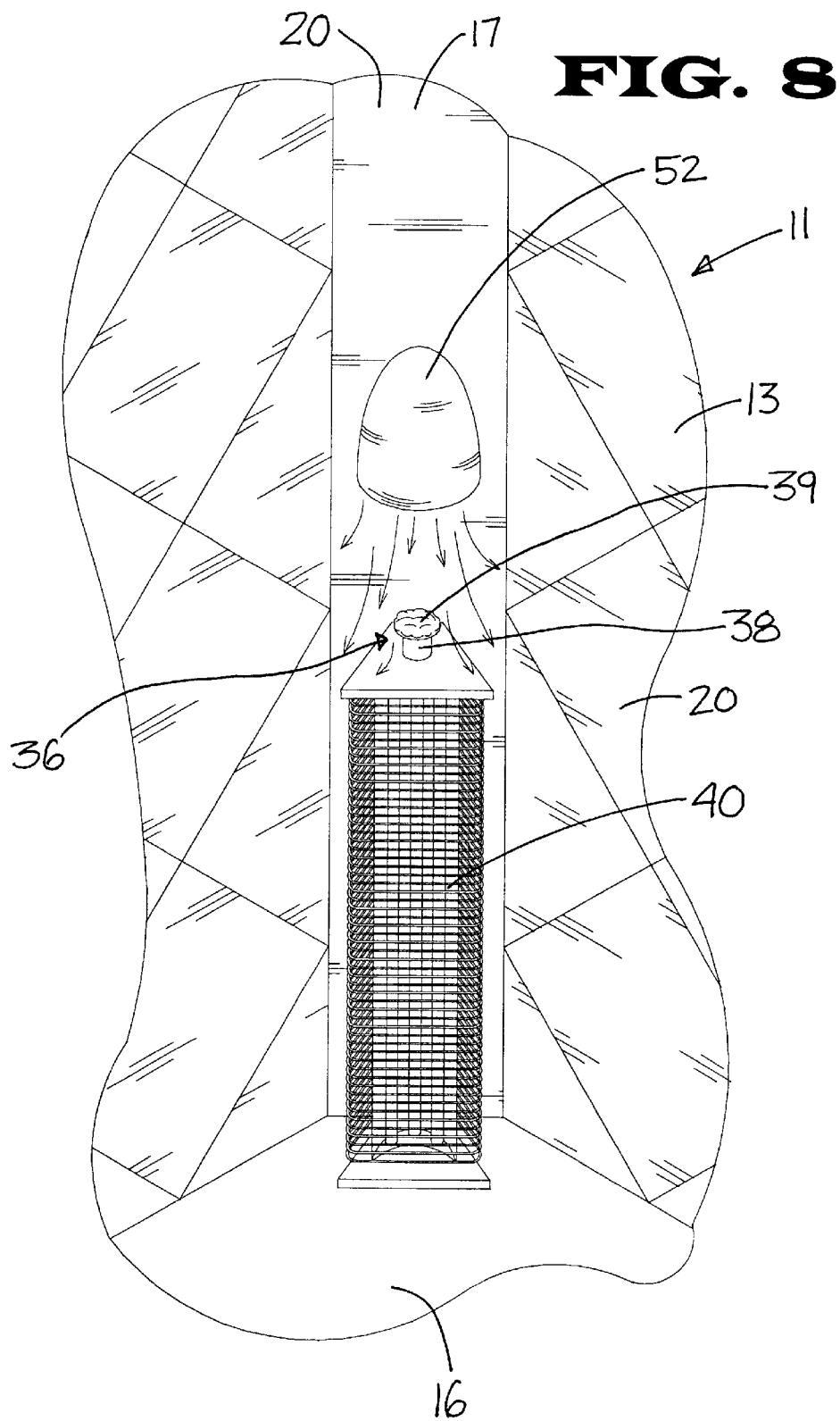
FIG. 8 is a perspective view of a portion of a room showing wall and transition faces with the panels of the present invention.
Figure 9:
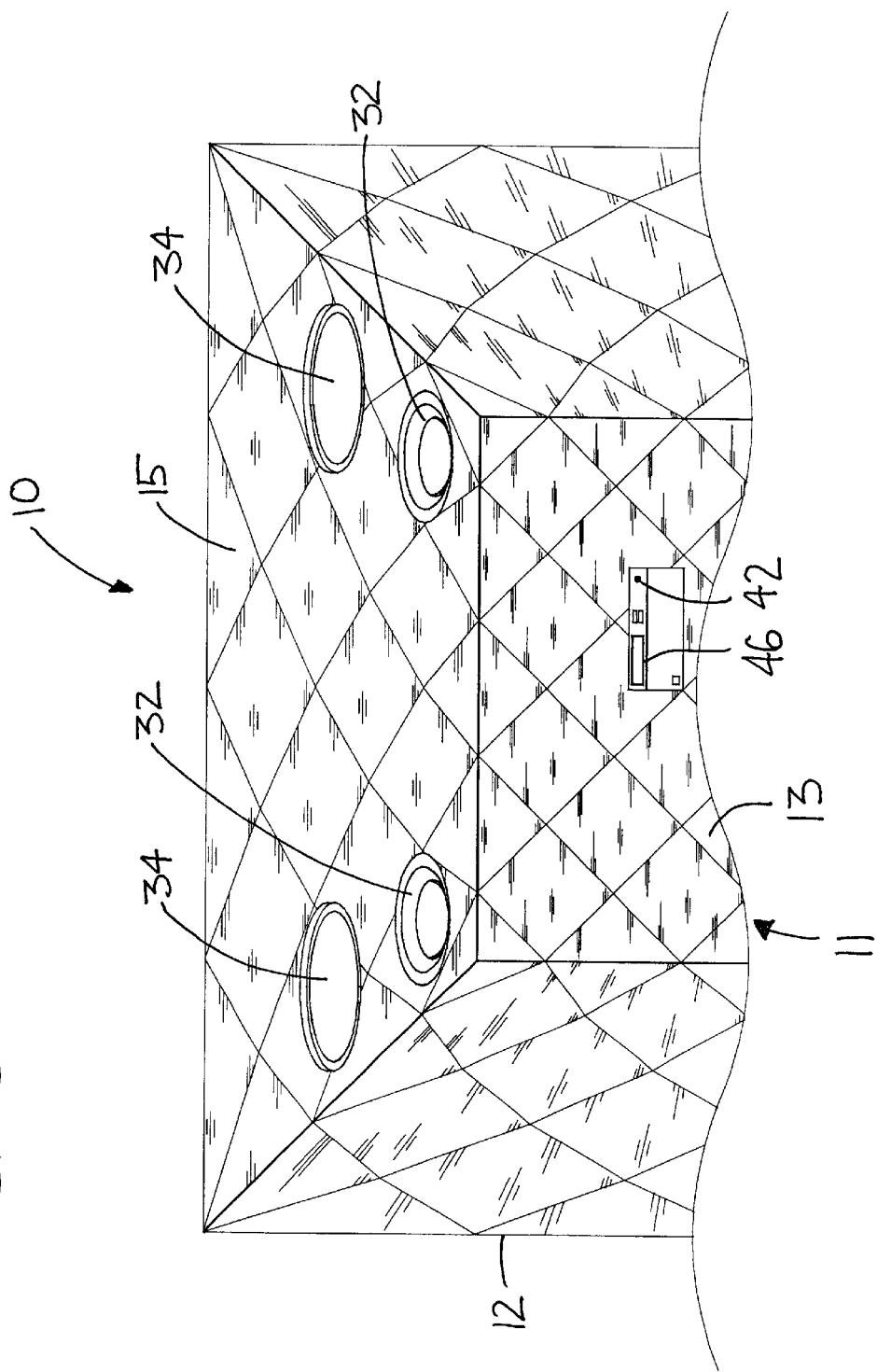
FIG. 9 is a perspective view of a portion of a room employing the present invention.

Optionally, a support rod 60 and a reflective curtain 70 may be provided to extend between corners of a room to provide a confined area for the user (FIG. 5). The support rod 60 may be adjustably extended between the walls 12 forming a corner. The reflective curtain 70 may be slidably attached about the support rod 60 (see FIG. 5). The reflective curtain 70 reflects the infrared lights waves that are emitted from the infrared heat emitters 40.

Figure 4:
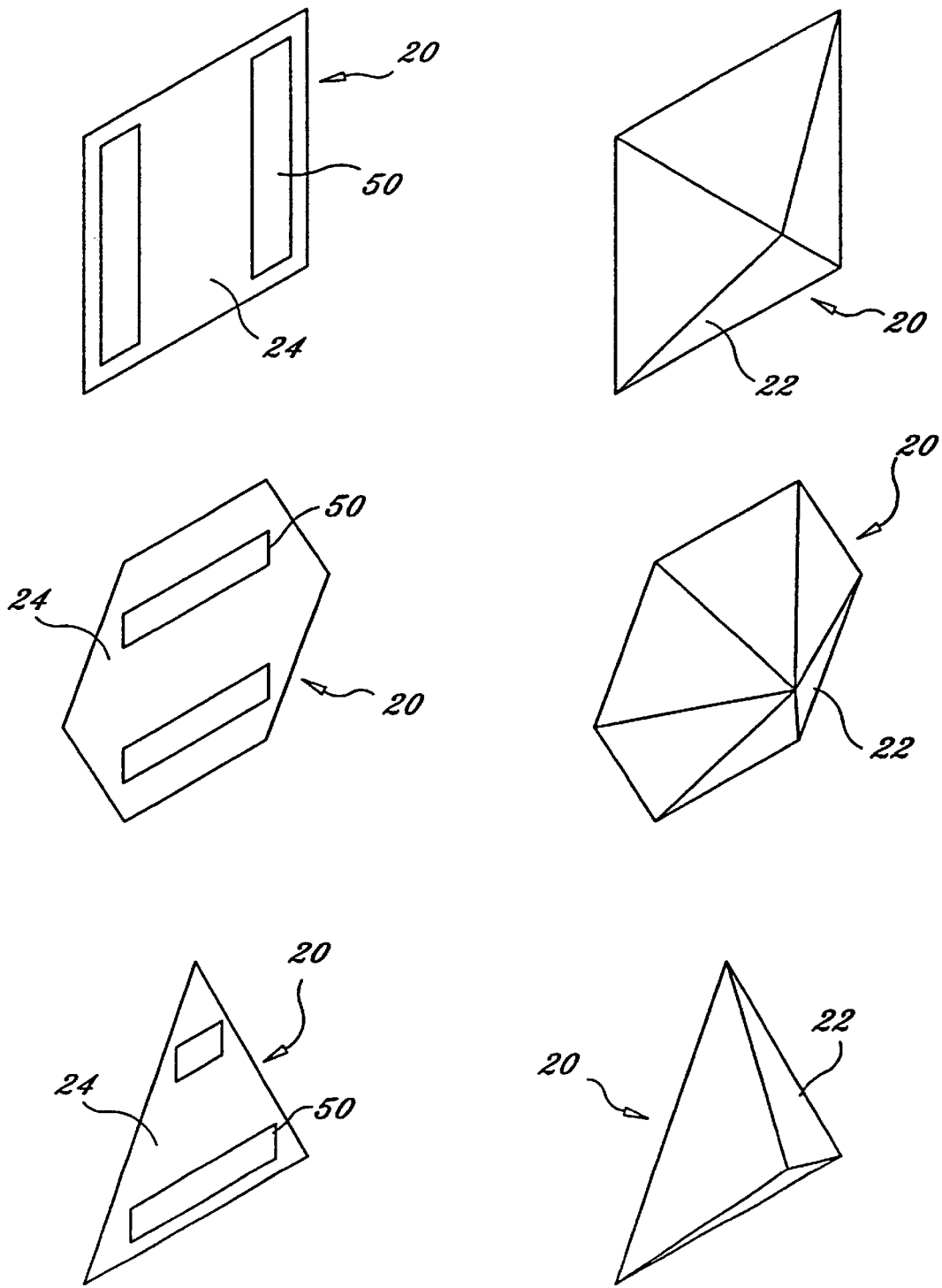
FIG. 4 is an upper perspective view showing various designs of the panels.

Optionally, the panels 20 may be constructed with perimeters of various geometric shapes such as square or triangular (see FIG. 4). As a further option, a design 26 may be engraved into the front surface 22 of the panels 20 (see FIG. 6) for providing an aesthetically pleasing appearance. In one aspect of the invention, the panels may have different colors on their surfaces, and the perimeters of the panels may be cut or formed to define various shapes on the face of the room and thereby depict scenes or logos, and the like.

As a further option, the user may also wear a reflective cap to cover a portion of their head to limit the exposure to infrared waves.

In use, the user may secure the plurality of panels 20 to the desired faces 12 of the room. The user secures the infrared heat emitters 40 to the faces 12 of the room for emitting the infrared radiation heat waves. The user adjusts the control unit 30 and positions his or her body within the interior of the room to receive the infrared heat waves from 360 degrees around their body. The skin of the user is deeply heated while the air within the room remains relatively cool compared to a conventional sauna, and also compared to infrared saunas in which the walls are covered with materials that exhibit relatively high emissivity characteristics. The panels 20 reflect the infrared heat waves about the room until they impinge on the user's body to thereby produce heat that causes the individual to perspire.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A spa system comprising:

a room of a structure having a plurality of faces defining a room interior space;

a plurality of panels each having a front surface and a rear, the front surface of each of the panels having an emissivity characteristic with respect to infrared radiation of from 0 to approximately 0.3;

securing means for securing each of the panels to one of the faces of the room, the securing means being positioned on the rear of each of the panels; and an infrared radiation emitter for generating infrared radiation and dispersing the radiation about the room interior space, the infrared wave source being positioned in the interior space such that infrared radiation generated by the infrared radiation emitter strikes the front surfaces of the plurality of panels;

wherein the plurality of faces includes wall faces of the room and the wall faces has at least one of the panels mounted thereon;

wherein the plurality of faces includes a plurality of transition faces, each of the transition faces extending between a pair of adjacent wall faces.

2. The spa system of claim 1 wherein each of the transition faces is positioned at an angle of approximately 45 degrees with respect to the adjacent wall faces.

3. A spa system comprising:

a room of a structure having a plurality of faces defining a room interior space;

a plurality of panels each having a front surface and a rear, the front surface of each of the panels having an emissivity characteristic with respect to infrared radiation from 0 to approximately 0.3;

securing means for securing each of the panels to one of the faces of the room, the securing means being positioned on the rear of each of the panels; and an infrared radiation emitter for generating infrared radiation and dispersing the radiation about the room interior space, the infrared wave source being positioned in the interior space such that infrared radiation generated by the infrared radiation emitter strikes the front surfaces of the plurality of panels;

wherein the front surface of each of the plurality of panels has an emissivity characteristic of from 0 to approximately 0.1;

wherein the front surface of the plurality of panels comprises a metal;

wherein the plurality of faces includes wall faces of the room and the wall faces has at least one of the panels mounted thereon;

wherein the plurality of faces includes a ceiling face and the ceiling face has at least one of the panels mounted thereon;

wherein the plurality of faces includes a plurality of transition faces, each of the transition faces being positioned at an angle of approximately 45 degrees with respect to the adjacent wall faces; and wherein the plurality of panels are arranged on the faces of the room such that the panels substantially cover each of the faces of the room such that the front surfaces of the plurality of panels are substantially continuous about the interior space of the room except for a floor of the room.

* * * * *